(12) United States Patent
Peyman et al.

(10) Patent No.: US 7,229,974 B2
(45) Date of Patent: *Jun. 12, 2007

(54) G CAP-STABILIZED OLIGONUCLEOTIDES

(75) Inventors: Anuschirwan Peyman, Kelkheim (DE); Eugen Uhlmann, Glashuetten (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 433 days.

This patent is subject to a terminal disclaimer.

(21) Appl. No.: 09/860,784

(22) Filed: May 21, 2001

(65) Prior Publication Data

US 2002/0151512 A1    Oct. 17, 2002

Related U.S. Application Data

(63) Continuation of application No. 09/631,946, filed on Aug. 3, 2000, now abandoned, which is a continuation of application No. 09/258,408, filed on Feb. 26, 1999, now Pat. No. 6,121,434, which is a continuation of application No. 08/594,452, filed on Jan. 31, 1996, now Pat. No. 6,013,639.

(30) Foreign Application Priority Data

Jan. 31, 1995 (DE) ............................... 195 02 912

(51) Int. Cl.
C07H 21/04 (2006.01)
A61K 31/70 (2006.01)
C12Q 1/68 (2006.01)

(52) U.S. Cl. .................... 514/44; 536/23.1; 536/24.1; 536/24.5; 435/6; 435/91.5

(58) Field of Classification Search ................ 435/6, 435/31.1, 325, 366, 375; 536/23.1, 24.3, 536/24.5, 24.31, 24.33; 935/33, 34; 514/44

See application file for complete search history.

(56) References Cited

U.S. PATENT DOCUMENTS

| | | | |
|---|---|---|---|
| 4,514,577 A | | 4/1985 | Filbey et al. |
| 5,514,577 A | * | 5/1996 | Draper et al. ................ 435/238 |
| 6,013,639 A | * | 1/2000 | Peyman et al. ................ 514/44 |
| 6,121,434 A | * | 9/2000 | Peyman et al. ............. 536/23.1 |

FOREIGN PATENT DOCUMENTS

| | | |
|---|---|---|
| CA | 2144475 | 9/1995 |
| EP | 0 552 766 A2 * | 1/1993 |
| EP | 0 552 766 | 7/1993 |

OTHER PUBLICATIONS

Koga et al., "Alternating α, β Oligothymidylates with Alternating (3'→3') and 5'→5')-Internucleotidic Phospodiester Linkages as Models for Antisense Oligodeoxyribonucleotides," Journal of Organic Chemistry, vol. 56, No. 12 pp. 3757-3759, Jun. 1991.

Hughes et al., "Influence of Base Composition on Membrane Binding and Cellular Uptake of 10-mer Phosphorothioate Oligonucleotides in Chinese Hamster Ovary ($CH^RC5$) Cells" Antisense Research and Development 4:211-215, 1994.

Uhlmann et al., "Oligonucleotide Analogs Containing Dephospho-Internucleoside Linkages", Methods in Molecular Biology, pp. 355-389, 1993.

Vandendriessche et al., "Acylic Oligonucleotides: Possibilities and Limitations", Tetrahedron vol. 49, No. 33, pp. 7223-7238, 1993.

Bock et al., "Selection of single-stranded DNA molecules that bind and inhibit human 000 thrombin", Nature vol. 355, pp. 564-566, Feb. 1992.

Castanotto et al., Biological and Funcational Aspects of Catalytic RNAs, Critical Reviews in Eukaryotic Gene Expressions, 2(4): 331-349, (1992).

Mann et al., "Synthesis and Properties of an Oligodeoxynucleotide Modified with a Pyrene Derivative at the 5'-Phosphate", Bioconjugate Chem., vol. 3. No. 6, pp. 554-558, 1992.

Sawadogo et al., "A rapid method for the purification of deprotected oligodeoxynucleotides", Nucleic Acids Research, vol. 19, No. 3, pp. 674, 1991.

Manohoran, "Designer Antisense Oligonucleotides: Conjugation Chemistry and Functionality Placement", Antisense Research and Applications, pp. 303-349, 1993.

Uhlmann et al., "Antisense Oligonucleotides: A New Therapeutic Principle", Chemical Reviews, vol. 90, No. 4, pp. 543-584, Jun. 1990.

Milligan et al., "Current Concepts in Antisense Drug Design", Journal of Medicinal Chemistry, vol. 36, No. 14, pp. 1923-1937, Jul. 9, 1993.

Bielinska et al., "Regulation of Gene Expression with Double-Stranded Phosphorothioate Oligonucleotides", Science, vol. 250, pp. 997-1,000, Nov. 1990.

Cooke, "Medicinal Chemistry Strategies for Antisense Research", Antisense Research and Applications, pp. 149-187, 1993.

Tang et al., "Self-stabilized antisense oligodeoxynucleotide phosphorothioates: properties and Anti-HIV activity", Nucleic Acids Research, vol. 21, No. 11, pp. 2729-2735, 1993.

Blackburn, "Structure and function of telomeres", Nature vol. 350, No. 18, pp. 569-573, Apr. 1991.

(Continued)

Primary Examiner—Sean McGarry

(57) ABSTRACT

Oligonucleotides of the formula

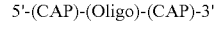

are disclosed where (oligo) is a nucleotide sequence of from 10 to 40 nucleotides in length, and CAP is $G_m$, where m is an integer of from zero to ten, the two CAP's which are present in the molecule can be defined independently of each other and must be different in the case where m is zero at the 5' or 3' end and the end of the Oligo sequence is other than guanine. The oligonucleotides can be synthesized chemically. The oligonucleotides are used to diagnose or treat cancer, restenosis, a disease caused by a virus, a disease affected by integrins or cell-cell adhesion receptor or a disease triggered by diffusible factors.

32 Claims, No Drawings

OTHER PUBLICATIONS

Stirchak et al., "Uncharged stereoregular nucleic acid analogs: 2. Morpholino nucleoside oligomers with carbamate internucleoside linkages", Nucleic Acids Research vol. 17, No. 15, pp. 6129-6141, 1989.

Nielsen et al., "Peptide Nucleic Acid (PNA). A DNA Mimic with a Peptide Backbone", Bioconjugate Chem., vol. 5, pp. 3-7, 1994.

Tarkoy et al., Nucleic—Acid Analogues with Constraint Conformational Flexibility in Sugar-Phosphate Backbone ('Bicyclo-DNA'), Helevetica Chimica Acta, vol. 76, pp. 481-510, 1993.

Froehler, "Triple-Helix Formation by Oligodeoxynucleotides Containing the Carbocyclic Analogs of Thymidine and 5-Methyl-2'-deoxycytidine", J. Am. Chem. Soc., vol. 114, pp. 8320-8322, 1992.

J. Goodchild, Bioconj, Chem. vol. 1(3): 165-87 "90.

D. Tidd et al., Brit. J. Cancer 60:343-50 '89.

T. Maniatis et al., Molecular Cloning a Lab Manual, Cold Spring Harbor Laboratory ('82), pp. 241-242, 390-391.

C. Stein et al., Science 261: 1004-12 '93.

B. Tseng et al., Cancer G. Therapy 1 (1): 65-71 '94.

R. Still et al., Pharm. Res. 12 (4) 465-83 '95.

* cited by examiner

SEQUENCE LISTING

```
<160> NUMBER OF SEQ ID NOS: 105

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acacccaatt ctgaaaatgg                                               20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aggtccctgt tcgggcgcca                                               20

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtcgacaccc aattctgaaa atggataa                                      28

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gctatgtcga cacccaattc tgaaa                                         25

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtcgctgtct ccgcttcttc ttcctg                                        26
```

-continued

```
<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtctccgctt cttcttcctg ccatagg                                27

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcggggctcc atggggtcg                                         20

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cagctgcaac ccagc                                             15

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggctgctgga gcggggcaca c                                      21

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aacgttgagg ggcat                                             15

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtgccggggt cttcgggc                                          18

<210> SEQ ID NO 12
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggagaacatc atggtcgaaa g                                            21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cccgagaaca tcatggtcga ag                                           22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggggaaagcc cggcaagggg                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cacccgcctt ggcctcccac                                              20

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gggactccgg cgcagcgc                                                18

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggcaaacttt cttttcctcc                                              20

<210> SEQ ID NO 18
<211> LENGTH: 19
```

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
gggaaggagg aggatgagg                                        19

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
ggcagtcatc cagcttcgga g                                     21

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
gcagtaagca tccatatc                                         18

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
cccccaccac ttcccctctc                                       20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
ctcccccacc acttcccctc                                       20

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
gctgggagcc atagcgagg                                        19

<210> SEQ ID NO 24
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 24
actgctgcct cttgtctcag g                                              21

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
caatcaatga cttcaagagt tc                                             22

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggtccctgtt cgggcgcca                                                 19

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtgccggggt cttcggg                                                   17

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggaggatgct gaggagg                                                   17

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggaggatgct gagg                                                      14

<210> SEQ ID NO 30
<211> LENGTH: 19
<212> TYPE: DNA
<213> ORGANISM: Artificial Sequence
```

-continued

<220> FEATURE:
<223> OTHER INFORMATION: Description of Artificial Sequence: Synthetic
      oligonucleotide

<400> SEQUENCE: 30
caggaggatg ctgaggagg                                                    19

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggctgccatg gtccc                                                        15

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tcatggtgtc ctttgcagcc                                                   20

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tcatggtgtc ctttgcag                                                     18

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aagttcatgg tttcgg                                                       16

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggggacaccc aattctgaaa atgggg                                            26

<210> SEQ ID NO 36
<211> LENGTH: 27
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 36
gggaggtccc tgttcgggcg ccagggg                                          27

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ggggtccctg ttcgggcgcc agggg                                            25

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggggtcgaca cccaattctg aaaatggata a                                     31

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gggtcgacac ccaattctga aaatggataa                                       30

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gctatgtcga cacccaattc tgaaagggg                                        29

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gctatgtcga cacccaattc tgaaaggg                                         28

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 42
gtcgctgtct ccgcttcttc ttcctgggg                    29

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gtcgctgtct ccgcttcttc ttcctggggg                   30

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gtcgctgtct ccgcttcttc ttcctggggg g                 31

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gtctccgctt cttcttcctg ccataggggg                   30

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gtctccgctt cttcttcctg ccatagggg                    29

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gcggggctcc atggggtcg gg                            22

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 48
ggcggggctc catgggggtc g                                              21

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggggaggatg ctgaggaggg gg                                             22

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ggggaggatg ctgaggaggg g                                              21

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gggggaggat gctgaggggg                                                20

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggggaggatg ctgaggggg                                                 19

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gggcaggagg atgctgagga ggggg                                          25

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 54 gggggcaggag gatgctgagg aggggg                                         26

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggggcagctg caacccagcg ggg                                             23

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gggcagctgc aacccagcgg gg                                              22

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggggctgctg gagcggggca cac                                             23

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ggggctgctg gagcggggca cacgggg                                         27

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ggggaacgtt gagggggcat                                                 19

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
```
ggggaacgtt gaggggcatg ggg                                           23

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ggggtgccgg ggtcttcggg c                                             21

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ggggtgccgg ggtcttcggg cgggg                                         25

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ggggtgccgg ggtcttcggg g                                             21

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gggggagaac atcatggtcg aaag                                          24

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gggggagaac atcatggtcg aaagggg                                       27

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66

```
ggggagaaca tcatggtcga aagggg                                      26
```

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67

```
ggagaacatc atggtcgaaa ggggg                                       25
```

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68

```
cccgagaaca tcatggtcga aggggg                                      26
```

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69

```
ggggaaagcc cggcaagggg g                                           21
```

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70

```
gggggaaagc cggcaagggg gg                                          22
```

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71

```
cacccgcctt ggcctcccac ggggg                                       25
```

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72

```
cacccgcctt ggcctcccac gggg                                        24
```

```
<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73 gggactccg gcgcagcgc                                                   19

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ggggactccg gcgcagcgcg ggg                                             23

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75 ggggactcc ggcgcagcgc gggg                                             24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76 ggggactcc ggcgcagcgc gggg                                             24

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ggggcaaact ttcttttcct ccgggg                                          26

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gggggaagga ggaggatgag g                                               21
```

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gggggaagga ggaggatgag gggg                                          24

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ggggcagtca tccagcttcg gag                                           23

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ggggcagtca tccagcttcg gagggg                                        26

<210> SEQ ID NO 82
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ggggctgcca tggtccc                                                  17

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ggggctgcca tggtcccggg g                                             21

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ggggaagttc atggtttcgg gg                                            22

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ggggcagtaa gcatccatat c                                              21

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ggggcagtaa gcatccatat cgggg                                          25

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ggggccccca ccacttcccc tctc                                           24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cccccaccac ttccctctc gggg                                            24

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ggggccccca ccacttcccc tctcgggg                                       28

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gggctccccc accacttccc ctcgggg                                        27

<210> SEQ ID NO 91

```
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ggctccccca ccacttcccc tcgggg                                        26

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ggggctggga gccatagcga gg                                            22

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ggggctggga gccatagcga gggg                                          24

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ggggctggga gccatagcga ggggg                                         25

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
actgctgcct cttgtctcag ggg                                           23

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ggggactgct gcctcttgtc tcagggg                                       27

<210> SEQ ID NO 97
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ggggcaatca atgacttcaa gagttc                                           26

<210> SEQ ID NO 98
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
caatcaatga cttcaagagt tcgggg                                           26

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ggggtcatgg tgtcctttgc agcc                                             24

<210> SEQ ID NO 100
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ggggtcatgg tgtcctttgc agccgggg                                         28

<210> SEQ ID NO 101
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ggggtcatgg tgtcctttgc agccggggg                                        29

<210> SEQ ID NO 102
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ggggtcatgg tgtcctttgc aggggg                                           26

<210> SEQ ID NO 103
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 103
tcatggtgtc ctttgcaggg gg                                              22

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gggggaggat gctgaggagg ggg                                             23

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gggggaggat gctgaggggg                                                 20
```

G CAP-STABILIZED OLIGONUCLEOTIDES

This application is a continuation of U.S. Ser. No. 09/631,946, filed Aug. 3, 2000 now abandoned, which is a continuation of U.S. Ser. No. 09/258,408, filed Feb. 26, 1999, which issued as U.S. Pat. No. 6,121,434, which is a continuation of U.S. Ser. No. 08/594,452, filed Jan. 31, 1996, which issued as U.S. Pat. No. 6,013,639. The entire contents of each of the above-identified applications are hereby incorporated by reference.

FIELD

The invention relates to oligonucleotides, particularly G Cap-stabilized oligonucleotides.

BACKGROUND

Antisense oligonucleotides (AO), triple helix-forming oligonucleotides (TFO) and sense oligonucleotides have been found to be specific inhibitors of gene expression in a large number of systems, both in vitro and in vivo (e.g., Uhlmann & Peyman, *Chem. Rev.*, 1990, 90: 543; Milligan et al., *J. Med. Chem.*, 1993, 36: 1923; Stein & Cheng, *Science*, 1993, 261: 1004; Bielinaki et al., *Science*, 1990, 250: 997).

One of the main problems when using naturally occurring phosphodiester (PO) oligonucleotides is their rapid degradation by various nucleolytic activities both in cells and in the cell culture medium. A variety of chemical modifications have been employed in order to stabilize oligonucleotides. Reviews on the state of the art are provided, for example, by Uhlmann & Peyman, above, and P. D. Cook (*Antisense Research and Applications*, Crooke and Lebleu, Eds., Chapter 9, p. 149ff, CRC Press Boca Raton 1993).

Stabilization against nucleolytic degradation can be effected by modifying or replacing the phosphate bridge, the sugar structural component or the nucleotide base, or by replacing the sugar-phosphate backbone of the oligonucleotides. Numerous modifications of the internucleoside bridge have, in particular, been described, since the phosphate bridge is the center of the nucleolytic attack. The nuclease-resistant inter-nucleoside bridges which are most frequently used are phosphorothioate (PS), methyl phosphonate (MeP) and phosphoramidate (PA) bridges. Hairpin or self-stabilized oligonucleotides, as described, for example, in Tang et al., *Nucl. Acids Res.*, 1993, 21: 2729) represent a further option for stabilization.

An additional problem in antisense technology is that cell penetration by the oligonucleotides is often inadequate. Numerous chemical modifications have been employed to improve this situation as well. Uhlmann & Peymann, above, and P. D. Cook, above, provide reviews of the state of the art. These modifications involve, inter alia, lipophilic conjugate groups at the 5' or 3' end of the oligonucleotide and neutral or ionic modifications of the backbone, and also 2' modifications on the pentofuranosyl ring. Hughes, *Antisense Research and Development*, 1994, 4: 211, demonstrates that the cell uptake of a 10-mer homo-G phosphorothioate is higher, by a factor of 2, than the cell uptake of the 10-mer homo-oligomeric phosphorothioate of T, A or C.

Blackburne, *Nature*, 1991, 350: 569, describes structures which can be assumed by G-rich oligonucleotides. In the presence of $Na^+$ or $K^+$, G-rich oligonucleotides which possess at least four short segments containing G residues are able to form intramolecular structures which contain so-called G quartets as the stabilizing element; these quartets comprise four guanine residues which are linked in one plane by way of Hoogsten base pairing. Several such elements are arranged one above the other. Frequently, oligonucleotides are too short to form such intramolecular structures. In these cases, G quartet structures can be formed by the association of two separate oligonucleotides.

SUMMARY

It has now been found that a very simple option exists for significantly improving unmodified or modified oligonucleotides with regard to their nuclease resistance and cell penetration, so that their activity is substantially improved, by extending the oligonucleotides at the 3' and/or 5' end by from one to 10 guanines.

Surprisingly, the novel oligonucleotides also exhibit a tendency to associate or aggregate. It is possible that they too form G quartet structures by the association of two or more oligonucleotides. Such structures would protect against exonuclease degradation and lead to an increased uptake into the cell. Since the associated structures are always also in equilibrium with the "free" oligonucleotides, sufficient "free" oligonucleotide should also always be available for regulating translation or transcription.

DETAILED DESCRIPTION

The invention relates to oligonucleotides of the formula:

where Oligo is, for example,

| | |
|---|---|
| ACACCCAATTCTGAAAATGG | (I), |
| AGGTCCCTGTTCGGGCGCCA | (II), |
| GTCGACACCCAATTCTGAAAATGGATAA | (III), |
| GCTATGTCGACACCCAATTCTGAAA | (IV), |
| GTCGCTGTCTCCGCTTCTTCTTCCTG | (V), |
| GTCTCCGCTTCTTCTTCCTGCCATAGG | (VI), |
| GCGGGGCTCCATGGGGTCG | (VII), |
| CAGCTGCAACCCAGC | (VIII), |
| GGCTGCTGGAGCGGGCACAC | (IX), |
| AACGTTGAGGGGCAT | (X), |
| GTGCCGGGGTCTTCGGGC | (XI), |
| GGAGAACATCATGGTCGAAAG | (XII), |
| CCCGAGAACATCATGGTCGAAG | (XIII), |
| GGGGAAAGCCCGGCAAGGGG | (XIV), |
| CACCCGCCTTGGCCTCCCAC | (XV), |
| GGGACTCCGGCGCAGCGC | (XVI), |
| GGCAAACTTTCTTTTCCTCC | (XVII), |
| GGGAAGGAGGAGGATGAGG | (XVIII), |
| GGCAGTCATCCAGCTTCGGAG | (XIX), |
| GCAGTAAGCATCCATATC | (XX), |
| CCCCCACCACTTCCCCTCTC | (XXI), |

-continued

| | |
|---|---|
| CTCCCCCACCACTTCCCCTC | (XXII), |
| GCTGGGAGCCATAGCGAGG | (XXIII), |
| ACTGCTGCCTCTTGTCTCAGG | (XXIV), |
| CAATCAATGACTRCAAGAGTTC | (XXV), |
| GGTCCCTGTTCGGGCGCCA | (XXVI), |
| GTGCCGGGTCTTCGGG | (XXVII), |
| GGAGGATGCTGAGGAGG | (XXVIII), |
| GGAGGATGCTGAGG | (XXIX), |
| CAGGAGGATGCTGAGGAGG | (XXX), |
| GGCTGCCATGGTCCC | (XXXI), |
| TCATGGTGTCCTTTGCAGCC | (XXXII), |
| TCATGGTGTCCTTTGCAG | (XXXIII), or |
| AAGTTCATGGTTTCGG | (XXXIV), | and CAP is $G_m$, where m is an integer of from zero to ten, preferably of from two to six, more preferably of from three to five and still more preferably four, and where the two CAP's which are present in the molecule can be defined independently of each other and must be different in the case where m is zero at the 5' or 3' end, wherein the end of the "Oligo" sequence is other than guanine.

In those cases in which the oligonucleotide (Oligo) ends at the 5' or 3' end with one or more guanines, it can be advantageous if CAP is $G_{(m-n)}$, where m in defined as above and n is the number of the guanines which naturally occur at the 5' or 3' end of the oligonucleotide (Oligo), and where (m-n) is preferably from two to six, more preferably from three to five, and still more preferably four.

The oligonucleotides which have been adapted in this way can be unmodified or modified, with the following variants being permitted:

a) Complete or partial replacement of the 3' and/or 5' phosphoric diester bridges, for example by a phosphorothioate, phosphorodithioate, ($NR^1R^2$)-phosphoramidate, boranophosphate, phosphate ($C_1$–$C_{21}$)-O-alkyl ester, phosphate [($C_6$–$C_{12}$) aryl-($c_1$–$c_{21}$)-O-alkyl ] ester, 2,2,2-trichlorodimethylethylphosphonate, ($C_1$–$C_8$) alkylphosphonate or ($C_6$–$C_{12}$)arylphosphonate bridge.

Replacement by a phosphorothioate, phosphorodithioate, $NR^1R^2$-phosphoramidate, phosphate O-methyl ester, phosphate O-ethyl ester, phosphate O-isopropyl ester, methylphosphonate or phenylphosphonate bridge in preferred. Replacement by a phosphorothioate, phosphorodithioate or methylphosphonate bridge is more preferred. Replacement by a phosphorothioate bridge is still more preferred.

$R^1$ and $R^2$ are, independently of each other, hydrogen or ($C_1$–$C_{18}$)-alkyl, ($C_6$–$C_{20}$)-aryl, ($C_6$–$C_{14}$)-aryl-($C_1$–$C_8$)-alkyl or -$(CH_2)_c$-$(NH(CH_2)_c)_d$-$NR^3R^3$, in which c is an integer of from 2 to 6, and d is an integer of from 0 to 6, and the $R^3$ groups are, independently of each other, hydrogen, ($C_1$–$C_6$)-alkyl or ($C_1$–$C_4$)-alkoxy- ($C_1$–$C_6$)-alkyl; $R^1$ and $R^2$ are preferably hydrogen, ($C_1$–$C_8$)-alkyl or methoxyethyl, more preferably hydrogen, ($C_1$–$C_4$)-alkyl or methoxyethyl. $R^1$ and $R^2$ can also, together with the nitrogen atom carrying them, form a 5–6-membered heterocyclic ring which can additionally contain a further heteroatom from the series O, S and N.

Preferably, one, two or three phosphoric diester bridges should be replaced at the 5' end and/or at the 3' end, preferably at the 5' end and at the 3' end. Preferably, the replacement of the phosphoric diester bridges should also be effected at the pyrimidine positions.

b) Complete or partial replacement of the 3' or 5' phosphoric diester bridges by "dephospho" bridges (see, for example, Uhlmann and Peyman in *Methods in Molecular Biology*, vol. 20: "Protocols for Oligonucleotides and Analogs", S. Agrawal, Ed., Humana Press, Totowa 1993, Chapter 16, 355ff), for example by formacetal, 3'-thio-formacetal, methylhydroxylamine, oxime, methylenedi-methylhydrazo, dimethylenesulfone or silyl groups. Replacement by formacetals and 3'-thioformacetals is preferred.

Preferably, one, two or three phosphoric diester bridges should be replaced at the 5' end and/or at the 3' end, preferably at the 5' end and at the 3' end. Preferably, the replacement of the phosphoric diester bridges should also be effected at the pyrimidine positions.

c) Complete or partial replacement of the sugar phosphate backbone, for example by "morpholinonucleoside" oligomers (see E. P. Stirchak et al., *Nucleic Acids Res.*, 1989, 17: 6129) or peptide nucleic acids (PNA's) (see P. E. Nielsen et al., *Bioconi. Chem.*, 1994, 5: 3) or else PNA/DNA hybrids as described in German Patent Application P 44 08 528.1.

d) Complete or partial replacement of the β-D-2'-deoxyribose units, for example by α-D-2'-deoxyribose, L-2'-deoxyribose, 2'-F-2'-deoxyribose, 2'-O-($C_1$–$C_6$)alkyl ribose, 2'-O-($C_2$–$C_6$)alkenyl ribose, 2'-$NH_2$-2'-deoxyribose, β-D-xylofuranose, α-arabinofuranose, 2,4-dideoxy-β-D-erythrohexopyranose, and carbocyclic (see Froehler, *J. Am. Chem. Soc.*, 1992, 114: 8320) and open-chain sugar analogs (see Vandendriesoche et al., *Tetrahedron*, 1993, 49: 7223) and bicyclo sugar analogs (see M. Tarkov et al., *Helv. Chim. Acta.*, 1993, 76: 481).

Replacement by 2'-F-2'-deoxyribose, 2'-O-($C_1$–$C_6$) alkyl ribose, 2'-O-($C_2$–$C_6$) alkenyl ribose or 2'-$NH_2$-2'-deoxyribose is preferred. Replacement by 2'-F-2'-deoxyribose, 2'-O-($C_1$–$C_4$) alkyl ribose, 2'-O-($C_2$–$C_4$) alkenyl ribose or 2'-$NH_2$-2'-deoxyribose is more preferred.

Replacement by 2'-O-methylribose, 2'-O-allylribose or 2'-O-butylribose is still more preferred.

Preferably, one, two or three ribose units should be replaced at the 5' end and/or at the 3' end, preferably at the 5' end and at the 3' end. Preferably, the replacement of the ribose units should also be-effected at the pyrimidine positions.

e) Complete or partial replacement of the natural nucleoside bases, for example by 5-(hydroxymethyl)uracil, 5-aminouracil, pseudouracil, dihydrouracil, 5-($C_1$–$C_6$)-alkyluracil, 5-($C_2$–$C_6$)-alkenyl-uracil, 5-($C_2$–$C_6$)-alkynyl-uracil, 5-($C_1$–$C_6$)-alkyl-cytosine, 5-($C_2$–$C_6$-alkenyl-cytosine, 5-($C_2$–$C_6$)-alkynyl-cytosine, 5-fluorouracil, 5-fluorocytosine, 5-chlorouracil, 5-chlorocytosine, 5-bromouracil, 5-bromocytosine or 7-deaza-7-substituted purines.

Replacement by 5-($C_1$–$C_6$)-alkyl-uracil, 5-($C_2$–$C_6$)-alkenyluracil, 5-($C_2$–$C_6$)-alkynyl-uracil, 5-($C_1$–$C_6$)-alkyl-cytosine, 5-($C_2$–$C_6$)-alkenyl-cytosine, 5-($C_2$–$C_6$)-alkynyl-cytosine, 5-fluorouracil, 5-fluorocytosine, 5-chloro-uracil, 5-chlorocytosine, 5-bromouracil, 5-bromocytosine, 7-deaza-7-alkynyl, preferably hexynyl-substituted purines, 7-deaza-7-methyl-substituted purines or 7-deaza-7-bromine-substituted purines is preferred. Replacement by 5-($C_3$–$C_6$)-alkyl-uracil, 5-($C_2$–$C_6$)-alkenyluracil, 5-($C_2$–$C_6$)-alkynyl-uracil, 5-($C_1$–$C_6$)-alkylcytosine, 5-($C_2$–$C_6$)-alkenyl-cytosine or 5-($C_2$–$C_6$)-alkynylcytosine is more preferred. Replacement by 5-hexynylcytosine, 5-hexynyluracil, 5-hexynylcytosine, 5-propynyluracil or 5-propynylcytosine is still more preferred.

The nucleoside bases should not be replaced in the CAP regions.

Of the above-mentioned modifications, those given in groups a), b), c) and d) are especially preferred. More preferred are those modifications given in groups a) and d), with those given in group a) being most preferred.

In addition, the novel oligonucleotides can be linked to (or conjugated with), for example at the 3' or 5' end, molecules which are known to have a favorable influence on the properties of antisense oligonucleotides or triple helix-forming oligonucleotides (such as, for example, cell penetration, nuclease degradation, affinity for the target RNA/DNA, and pharmacokinetics). Examples are conjugates with polylysine, with intercalators such as pyrene, acridine, phenazine and phenanthridine, with fluorescent compounds such as fluorescein, with cross-linkers such as psoralene and azidoproflavin, with lipophilic molecules such as ($C_{12}$–$C_{20}$)-alkyl, with lipids such as 1,2-dihexadecyl-rac-glycerol, with steroids such as cholesterol or testosterone, with vitamins such an vitamin E, with polyethylene glycol or oligoethylene glycol, with ($C_{12}$–$C_{18}$)-alkyl-phosphate diesters, and with —O—$CH_2$—CH (OH)—O—($C_{12}$–$C_{18}$)—alkyl. Conjugates with lipophilic molecules, such as ($C_{12}$–$C_{20}$)-alkyl, with steroids, such as cholesterol or testosterone, with polyethylene glycol or oligoethylene glycol, with vitamin E, with intercalators, such as pyrene, with ($C_{14}$–$C_{18}$)-alkyl-phosphate diesters and with —O—$CH_2$—CH(OH)—O—($C_{12}$–$C_{16}$)-alkyl are preferred. Those skilled in the art are familiar with the preparation of such oligonucleotide conjugates (see, for example, Uhlmann & Peyman, *Chem. Rev.*, 1990, 90: 543; M. Manoharan in *Antisense Research and Applications*, Crooke and Lableu, Eds., CRC Press, Boca Raton, 1993, Chapter 17, p. 303ff; and EP 0552766A2).

Furthermore, the novel oligonucleotides can carry 3'—3' and 5'—5' inversions at the 3' and/or the 5' end (described, for example, in M. Koga et al., *J. Org. Chem.*, 1991 56: 3757).

The invention also relates to a process for preparing the novel compounds using methods, in particular chemical synthesis, the individual and separate steps of which are known to a person skilled in the art, as well as to the use of the novel compounds for preparing a pharmaceutical and also to a process for preparing a pharmaceutical which comprises mixing the novel oligonucleotides with a physiologically acceptable excipient and, where appropriate, suitable additives and/or auxiliary substances.

In a quite general manner, the present invention also extends to the use of therapeutically effective oligonucleotides, in which at least one non-terminal pyrimidine nucleoside is modified, for preparing the pharmaceutical. In general, therapeutically effective oligonucleotides are understood to mean antisense oligonucleotides, triple helix-forming oligonucleotides, aptamers (RNA or DNA molecules which are able to bind to specific target molecules, for example proteins or receptors, e.g., L. C. Bock et al., *Nature*, 1992, 355: 564, or ribozymes (catalytic RNA), e.g., Castanetto et al., *Critical Rev. Eukar. Gene Expr.*, 1992, 2: 331), in particular antisense oligonucleotides.

In addition to this, the present invention also relates to the use of oligonucleotides possessing at least one terminal and modified pyrimidine nucleoside as diagnostic agents, for example for detecting the presence or absence, or the quantity, of a specific double-stranded or single-stranded nucleic acid molecule in a biological sample.

For use according to the invention, the oligonucleotides have a length of from about 6 to 60, preferably of from about 10 to 40, in particular of from about 12 to 31, nucleotides. Otherwise, the above-described preference ranges, modifications and/or conjugations also apply here.

The pharmaceuticals of the present invention may be used, for example, for treating diseases which are caused by viruses, for example by HIV, HSV-1, HSV-2, influenza, VSv, hepatitis B or papilloma viruses.

Examples of novel antisense oligonucleotides which are effective against these targets are:

```
a) against HIV, e.g.

5'-G★G★G★G A C A C C C A A T T C T G A A A A T G★G★G★G-3' or

5'-G★G★G★G A C A C C★C A A T★T C★T G A A A A T G★G★G★G-3' or

5'-G★G★G G A C A C★C★C A A T T C T G A A A A T G★G★G★G-3'

(SEQ ID NO: 35)

5'-G★G★G★A G G T★C C★C★T G T★T★C G G G C G C★C A G★G★G★G-3' or

5'-G★G★G★A G G T★C C★C★T G★T T★C G G G C G C★C★A★G★G★G★G-3'

(SEQ ID NO: 36)

5'-G★G★G★G T★C C★C★T G T★T★C G G G C G C★C★A★G★G★G★G-3'

(SEQ ID NO: 37)

5'-G★G★G G T★C G A★C A C★C C A A T★T C★T G A A A A T★G A T★A★A-
3' or

5'-G★G★G G T★C G A★C A C★C★C A A T★T C★T G A A A A T★G A T★A★A-
3' or

5'-G★G★G G T★C G A★C A C★C★C A A T★T C★T G A A A A T★G G A★T★A★A-
3' or
```

-continued

5'-G★G★G T★C★G A★C A C★C★C A A T★T★C★T G A A A A T★G G A★T★A★A-3'

(SEQ ID NO: 38–39)

5'-G★C★T A T G T★C G A★C A C C★C A A T★T★C★T★G A A A G★G★G★G-3' or

5'-G★C★T A T★G T★C G A★C A C C★C A A T★T★C★T★G A A A G★G★G★G-3' or

5'-G★C★T A T★G T★C G A C A C★C C★A A T★T C★T G A A A G★G★G★G-3' or

5-G★C★T A T★G T★C G A C★A C★C C★A A T★T C★T G A A A G★G★G★G-3' or

5'-G★C★T A T G T★C G A C A C★C C★A A T★T C★T G A A A G★G★G-3'

(SEQ ID NO: 40–41)

5'-G★T★C G C★T G T C★T★C★C G C T★T C T T C T T C C★T G★G★G★G-3' or

5'-G★T★C G C★T G T C★T★C★C G C T★T C T T C T T C C★T G G★G★G★G-3' or

5'-G★T★C G C★T G T C★T★C★C G C T★T C T T C T T C C★T G G★G★G★G★G-3' or (SEQ ID NO: 42–44)

5'-G★T★C★T C★C G C T★T C★T T★C T★T C★C T G C★C A T A G G★G★G★G-3' or

5'-G★T★C★T C★C C C T★T C★T T★C T★T C★C T G C★C A T A G★G★G★G-3' or (SEQ ID NO: 45–46)

b) against HSV-1, e.g.

5'-G★C★G G G G C T C C★A T G G G G G T★C★G★G-3' or

5'-G★G★C★G G G G C★T C C A★T G G G G G T★C★G-3' or (SEQ ID NO: 47–48)

5'-G★G★G★G A G G A T★G C★T★G A G G A G G★G★G★G-3' or

5'-G★G★G★G A G G A T★G C★T★G A G G A G G★G★G-3' or (SEQ ID NO: 49–50)

5'-G★G★G★G G A C C A T★G C★T G A G G★G★G★G-3' or

5'G★G★G G A G G A T★G C★T G A G G★G★G★G-3' or (SEQ ID NO: 51–52)

5'-G★G★G★C A G G A G G A T★G C★T★G A G G A G G★G★G★G-3' or

5-G★G★G★G★C A G G A G G A T★G C★T★G A G G A G G★G★G★G-3'.

(SEQ ID NO: 53–54)

The arabic numbers which are given here refer to the Roman numbers given earlier; the oligonucleotides which are listed above are additionally provided with the novel CAP'S.

In the above sequences, the phosphoric diester bonds which were replaced by a phosphorothioate bridge (P=S) were labeled with an asterisk (*).

The pharmaceuticals of the present invention are also suitable, for example, for treating cancer or restenosis. For example, oligonucleotide sequences may be used in this context which are directed against targets which are responsible for the genesis or growth of cancer.

Examples of these targets are:

1) Nuclear oncoproteins such as, for example, c-myc, N-myc, c-myb, c-fos, c-fos/jun, PCNA and p120;

2) Cytoplasmic/membrane-associated oncoproteins such as, for example, EJ-ras, c-Ha-ras, N-ras, rrg, bcl-2, cdc-2, c-raf-l, c-mos, c-src and c-abl;

3) Cellular receptors such as, for example, EGF receptor, c-erbA, retinoid receptors, protein kinase regulatory subunit and c-fms; and 4) Cytokines, growth factors and extracellular matrix such as, for example, CSF-1, IL-6, IL-1a, IL-1b, IL-2, IL-4, bFGF, myeloblastin, fibronectin and VEGF (vascular endothelial growth factor).

Examples of novel antisense oligonucleotides which are effective against these targets are:

a) against c-Ha-ras, e.g.

a) against c-Ha-ras, e.g.

5'-G★G★G★G C A G C★T G★C A A C★C★C A G★C G★G★G★G-3' or

5'-G★G★G★C A G C★T G★C A A C★C★C A G★C G★G★G★G-3' or

5'-G★G★G★G★C★A★G★C★T★G★C★A★A★C★C★C★A★G★C★G★G★G★G-3' or (SEQ ID NO: 55–56)

b) c-myc, e.g.

5'-G★G★G★G C★T C C★T G G A G★C G G G G★C A C★A★C-3' or

5'-G★G★G★G C★T G C★T G G A G★C G G G G★C A C★A★C★G★G★G★G-3' or

5'-G★G★G★G★G★C★T★G★C★T★G★G★A★G★C★G★G★G★G★G★C★A★C★A★C-3' or (SEQ ID NO: 57–58)

5'-G★C★G★G A A★C G T★T C A G G G G C★A★T-3' or

5'-G★G★G★G A A★C G T★T G A G G G G C★A★T G★G★G★G-3' or (SEQ ID NO: 59–60)

c) c-myb, e.g.

5'-G★G★G★G T★G C★C G G G G T★C★T★T C G G★G★C-3' or

5'-G★G★G★G T★G C★C G G G G T★C★T★T C G G★G★C G★G★G★G-3' or (SEQ ID NO: 61–62)

5'-G★G★G★G T★G C★C★G G G G T★C T★T★C G G★G★G★G-3' or (SEQ ID NO: 63)

(d) c-fos, e.g.

5'-G★G★G★G G A G A A C★A T★C A T★G G T★C G A A★A★G-3' or

5'-G★G★G★G G A G A A C★A T★C A T★G G T★C G A A A G★G★G★G-3' or

5'-G★G★G★G A G A A C★A T★C A T★G G T★C G A A A G★G★G★G-3' or

5'-G★G★A G A A C★A★T★C A T★G G T★C G A A★A★G★G★G★G-3' or (SEQ ID NO: 64–67)

5'-C★C★C★G A G A A★C A T★C A T★G G T★C G A★A★G★G★G★G★G-3' or (SEQ ID NO: 68)

5'-G★G★G G A A A G C★C★C G G★C A A G G★G★G★G-3' or

5'-G★G★G★G G A A A G C★C C★G G C★A A G G★G★G★G-3'

(SEQ ID NO: 69–70)

-continued e) p120, e.g.

5'-C★A★C★C C★G C★C T★T G G C C T★C C★C A★C G G★G★G★G-3' or

5'-C★A★C★C C★G C★C T★T G G C★C T★C C★C A★C G G★G★G-3' or (SEQ ID NO: 71–72)

f) EGF receptor, e.g.

5'-G★G★G★G A C★T★C★C G G★C G★C A G C★G★C-3' or

5'-G★G★G★G A C★T★C★C G G★C G★C A G C★G★C G★G★G★G-3' or

5'-G★G★G G G A C★T★C★C G G★C G★C A G C★G★C G G★G★G-3' or (SEQ ID NO: 73–75)

5'-G★G★G★G C A A A C T★T★T C T T★T★T C C T★C★C-3' or

5'-G★G★G★G C A A A C T★T★T C T T★T★T C C T★C★C G G★G★G-3' or (SEQ ID NO: 76–77)

g) p53 tumor suppressor, e.g.

5'-G★G★G G G A A G G A G G A G G A T★G A★G★G-3' or

5'-G★G★G G G A A G G A G G A G G A T★G A G G G★G★G-3' or (SEQ ID NO: 78–79)

5'-G★G★G★G★G★C A G T★C A T★C★C A G C★T T★C G G★A★G-3' or

5'-G★G★G G★C A G T★C A T★C★C A G C★T T★C G G A G★G★G★G-3' or (SEQ ID NO: 80–81)

h) bFGF, e.g.

5'-G★G★G G C★T G C C A★T G G T★C★C★C-3' or

5-G★C★G★G C★T G C C A★T G G T★C C★C G★G★G★G-3' or (SEQ ID NO: 82–83)

i) VEGF, e.g.

5'-G★G★G★G A A C T★T★C A★T G G T★T★T C G★G★G★G-3'.

(SEQ ID NO: 84)

The pharmaceuticals of the present invention are furthermore suitable, for example, for treating diseases which are influenced by integrins or cell-cell adhesion receptors, for example by VLA-4, VLA-2, ICAM or ELAM.

Examples of novel antisense oligonucleotides which are effective against these targets are:

a) VLA-4, e.g.

5'-G★G★G★G C★A G★T A A G C★A T★C★C A T★A★T★C-3' or

5'-G★G★G★G C★A G★T A A G C★A T★C★C A T★A T★C G★G★G★G-3' or (SEQ ID NOS 85–86)

b) ICAM, e.g.

5'-G★G★G★G★C★C★C C C A C★C A C T★T★C★C C C T C★T★C-3' or

5'-C★C★C★C C A C★C A C T★T★C★C C C T★C★T★C★G★G★G★G-3' or

-continued

5'-G★G★G★G★C★C★C★C  C  A  C★C  A  C  T★T★C★C  C  C
T★C★T★C★G★G★G★G-3' or (SEQ ID NOS 87–89)

5'-G★G★G★C★T★C★C C C C A C★C A C T★T C C C★C★T★C★G★G★G★G-3' or

5'-G★G★C★T★C★C C C C A C★C A C T★T C C C★C★T★C★G★G★G★G-3' or (SEQ ID NOS 90–91)

5'-G★G★G★G★C★T G G G A G C★C A★T A G★C G A★G★G-3' or

5'-G★G★G★G★C★T G G G A G C★C A★T A G★C G A★G★G★G★G-3' or

5'-G★G★G G★C★T G G G A G★C★C A★T A G★C G A G G★G★G★G★3' or (SEQ ID NOS 92–94)

c) ELAM-1, e.g.

5'-A★C★T G C★T G C★C T★C T★T G T★C T★C A★G★G★G★G-3' or

5'-G★G★G★G A C★T G C★T G C★C T★C T★T G T★C T★C A G G★G★G★3' or (SEQ ID NOS 95–96)

5'-G★G★G★G C★A A T★C A A T★G A C★T T★C A A G A G T★T★C-3' or

5'-C★A★A T C A A T★G A C★T T★C A A G A G T★T★C G G★G★G-3'

(SEQ ID NOS 97–98)

The pharmaceuticals of the present invention are also suitable, for example, for treating diseases which are triggered by factors such as TNF-alpha.

Examples of novel antisense oligonucleotides which are effective against these targets are:

a) TNF-alpha, e.g.

5'-G★G★G★G T C A T G G★T G T C★C T★T T G C A★G★C★C-3' or

5'-G★G★G★G T★C A★T G G★T G T C★C T★T★T G★C A G C★C G★G★G★G-3' or

5'-G★G★G★G T★C A★T G G★T G T C★C T★T★T G★C A G C★C G G★G★G★G-3' or (SEQ ID NOS 99–101)

5'-G★G★G★G T★C A★T G G★T G T C★C T★T★T G★C A G G★G★G★G-3' or

5'-T★C★A★T G G★T G★T C★C T★T★T G★C A G G★G★G★G-3'
SEQ ID NOS (102–103)

That which has been stated above applies with regard to the numbering of the exemplary oligonucleotides and the asterisk symbol. The novel oligonucleotides can also be used to prepare one diagnostic agent at least for all the diseases mentioned.

The pharmaceuticals may be used, for example, in the form of pharmaceutical preparations which can be administered orally, for example in the form of tablets, coated tablets, hard or soft gelatin capsules, solutions, emulsions or suspensions. They may also be administered rectally, for example in the form of suppositories, or parenterally, for example in the form of injection solutions. For producing pharmaceutical preparations, these compounds can be worked into therapeutically inert, organic and inorganic excipients. Examples of such excipients for tablets, coated tablets and hard gelatin capsules are lactose, corn starch or derivatives thereof, tallow and stearic acid or salts thereof. Suitable excipients for preparing solutions are water, polyols, sucrose, invert sugar and glucose. Suitable excipients for injection solutions are water, alcohols, polyols, glycerol and vegetable oils. Suitable excipients for suppositories are vegetable and hardened oils, waxes, fats and semiliquid polyols.

The pharmaceutical preparations can also contain preservatives, solvents, stabilizers, wetting agents, emulsifiers, sweeteners, dyes, flavorants, salts for altering the osmotic pressure, buffers, coating agents, antioxidants and, where appropriate, other therapeutically active compounds.

Oral administration and injections are preferred. For injection, the antisense oligonucleotides are formulated in a liquid solution, preferably in a physiologically acceptable buffer such as, for example, Hank's solution or Ringer's solution. However, the antisense oligonucleotides can also be formulated in solid form and dissolved or suspended before use. The doses which are preferred for the systemic administration are from about 0.01 mg/kg to about 50 mg/kg of body weight and per day.

The invention is further illustrated by, though in no way limited to, the following examples. Table 1 shows oligonucleotides which have been tested for their in vitro activity against HSV-1. Oligonucleotide no. 4 is modified as described in Mann et al. (*Bioconj. Chem.,* 1992, 3: 554) by the introduction of a (4-(1-pyrenyl)butanyl)phosphodiester at the 5' end. The novel oligonucleotides exert an effect at a minimum inhibitory concentration which is as low as 9 µM (Examples 1 and 4) or even 3 µM (Examples 2 and 3).

EXAMPLE 1

Oligonucleotide Synthesis

Unmodified oligonucleotides were synthesized on an automatic DNA synthesizer (Applied Biosystems, model 380B or 394) using standard phosphoramidite chemistry and oxidizing with iodine. For introducing phosphorothioate bridges in mixed phosphorothioates and phosphodiester oligonucleotides, oxidation was carried out with TETD (tetraethylthiuram disulfide) instead of with iodine (Applied Biosystems User Bulletin 65). Following cleavage from the solid support (CPG or Tentagel) and removal of the protective groups with conc. $NH_3$ at 55° C. for 18 h, the oligonucleotides were initially purified by butanol precipitation (Sawadogo, Van Dyke, *Nucl. Acids Res.,* 1991, 19: 674). The sodium salt was then obtained by precipitating from a 0.5 M NaCl solution containing 2.5 parts by volume of ethanol.

The oligonucleotides were analyzed by a) analytical gel electrophoresis in 20% acrylamide, 8 M urea, 45 mM Tris-borate buffer, pH 7.0, and/or b) HPLC analysis: Waters GenPak FAX, gradient $CH_3CN$ (400 ml), $H_2O$ (1.6 l), $NaH_2PO_4$ (3.1 g), NaCl (11.7 g), pH 6.8 (0.1 M with respect to NaCl) after $CH_3CN$ (400 ml), $H_2O$ (1.6 l), $NaH_2PO_4$ (3.1 g), NaCl (175.3 g), pH 6 8 (1.5 M with respect to NaCl), and/or c) capillary gel electrophoresis, Beckman capillary tube eCAP™, U100P gel column, 65 cm length, 100 mm I.D., window 15 cm from one end, buffer 140 µM Tris, 360 mM boric acid, 7M urea, and/or d) electrospray mass spectroscopy.

The analysis of the oligonucleotides indicated that each of them was more than 90% pure.

EXAMPLE 2

Investigation of the In-vitro Antiviral Activity of Test Substances Against Herpes Viruses The antiviral activity of the test substances against various herpes viruses which are pathogenic to humans is investigated in a cell culture test system. For the experiment, monkey kidney cells (Vero, $2 \times 10^5$/ml) in serum-containing Dulbecco's MEM (5% fetal calf serum (FCS)) are sown in 96-well microliter plates, which are incubated at 37° C. for 24 h in 5% $CO_2$. The serum-containing medium is then sucked off and the cells are rinsed twice with serum-free Dulbecco's MEM.

The test substances are prediluted in $H_2O$ to a concentration of 600 µM, and the solutions are stored at −18° C. For the test, further dilution steps are carried out in Dulbecco's minimal essential medium (MEM). 100 µl of each of the individual test substance dilutions are added, together with 100 µl of serum-free Dulbecco's MEM (-FCS), to the rinsed cells. After 3 h of incubation at 37° C. and in 5% $CO_2$, the cells are infected with herpes simplex virus type 1 (ATCC VR733, HSV-1 F strain) or with herpes simplex virus type 2 (ATCC VR734, HSV-2 G strain) in concentrations at which the cell lawn is completely destroyed within 3 days. In the case of HSV-1, the infection intensity is 500 plaque-forming units (PFU) per well, while in the case of HSV-2 it is 350 PFU/well. The experimental mixtures then contain test substance at concentrations of from 80 µM to 0.04 µM in MEM, supplemented with 100 U/ml penicillin G and 100 mg/l streptomycin. All the experiments are carried out as duplicate determinations apart from the controls, which are carried out eight times per plate.

The experimental mixtures are incubated at 37° C. for 17 h in 5% $CO_2$. The cytotoxicity of the test substances is determined after a total incubation time of 20 h by microscopic assessment of the cell cultures. The highest preparation concentration which still does not elicit any microscopically recognizable cell damage under the stated experimental conditions is designated the maximum tolerated dose (MTD).

After this, FCS is added to a final concentration of 4% and the plates are incubated for a further 55 h at 37° C. in 5% $CO_2$. The untreated infection controls then exhibit a fully developed cytopathic effect (CPE). After the cell cultures have been assessed microscopically, they are then stained with neutral red in accordance with the vital staining method of Pinter (1966). The antiviral activity of a test substance is defined as the minimum inhibitory concentration (MIC) which is required in order to protect 30–60% of the cells from the cytopathogenic effect due to virus.

Table 1 shows the activity of variously modified antisense oligonucleotides against HSV-1 in cell culture. The phosphodiester bonds which were replaced by a phosphorothioate bridge (P=S) were labeled with an * in the sequences; MIC=minimum inhibitory concentration; MTD=maximum tolerated dose; Py=pyrene.

TABLE 1

| Sequence | MIC | MTD | |
|---|---|---|---|
| 5'-G★G★G★C A G G A G G A T★G C★T★G A G G A G G★G★G★G | 9 | >80 | (SEQ ID NO:53) |
| 5'-G★G★G★G G A G G A T★G C★T★G A G G A G G★G★G★G | 3 | >80 | (SEQ ID NO:104) |
| 5'-G★G★G★G G A G G A T★G C★T G A G G★G★G★G | 3 | >80 | (SEQ ID NO:51) |
| 5'-PY-G★G★G★G G A G G A T★G C★T G A G G★G★G★G | 9 | >80 | (SEQ ID NO:105) |

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually. The disclosure of German Patent Application No. 195 02 912.7, for which benefit under 35 USC § 119 is claimed, is expressly incorporated herein in its entirety.

What is claimed is:

1. An oligonucleotide of the formula

5'-(CAP)-(Oligo)-(CAP)-3' wherein the Oligo is a nucleotide sequence between 10 to 40 nucleotides in length whose 5' end and 3' end are Gn, where n is an integer between 0 to 40 and is the number of guanines which occurs at the 5' or 3' end of the Oligo, wherein each CAP is G(m-n) where m is an integer and is defined independently of each other, wherein the a 3' or 5' phosphoric diester bridge in each CAP is completely or partially replaced by phosphorothioate bridges, wherein (i) m is no greater than ten and may not be zero at both the 5' and 3' ends when n is zero at both the 5' and 3' ends of the Oligo and, (ii) m-n is zero when n is no smaller than ten at either the 5' or 3' end of the Oligo, wherein Oligo is ACACCCAATTCTGAAAATGG (SEQ ID NO: 1).

2. The oligonucleotide as claimed in claim 1, wherein m is from two to six.

3. The oligonucleotide as claimed in claim 2, wherein m is from three to five.

4. The oligonucleotide as claimed in claim 3, wherein m is four.

5. The oligonucleotide as claimed in claim 1, further comprising a modification selected from the group consisting of: (a) complete or partial replacement of the 3' and/or 5' phosphoric diester bridges, (b) complete or partial replacement of the 3' and/or 5' phosphoric diester bridges by dephospho bridges, (c) complete or partial replacement of the sugar phosphate backbone, (d) complete or partial replacement of the .beta.-D-2'-deoxyribose units, and (e) complete or partial replacement of the natural nucleoside bases.

6. The oligonucleotide as claimed in claim 5, wherein the modification is selected from the group consisting of (a) complete or partial replacement of the 3' and/or 5' phosphoric diester bridges by a member selected from the group consisting of phosphorothioate, phosphorodithioate, $(NR^1R^2)$-phosphoramidate, boranophosphate, phosphate-$(C_1-C_{21})$-O-alkyl ester, phosphate$[(C_6-C_{12})$-aryl-$(C_1-C_{21})$-O-alkyl]$ ester, 2,2,2-trichlorodimethylethylphosphonate, $(C_1-C_8)$-alkylphosphonate and $(C_6-C_{12})$-arylphosphonate bridge, where $R^1$ and $R^2$ are, independently of each other, hydrogen, or $(C_1-C_{18})$-alkyl, $(C_6-C_{20})$-aryl, $(C_6-C_{14})$-aryl-$(C_1-C_8)$-alkyl or —$(CH_2)_c$-[NH(CH$_2$)$_c$]$_d$NR$^3$R$^3$, in which c is an integer of from 2 to 6, d is an integer of from 0 to 6, the $R_3$ groups are, independently of each other, hydrogen, $(C_1-C_6)$ alkyl or $(C_1C_4)$-alkoxy-$(C_1-C_6)$-alkyl, R and R are independently hydrogen, $(C_1-C_8)$-alkyl or methoxyethyl, or $R^1$ and $R^2$ together with the nitrogen atom carrying them, form a 5-6-membered heterocyclic ring which can additionally contain a further O, S, or N hetero atom; (b) replacement of one, two or three of the 3' and/or 5' phosphoric diester bridge(s) by dephospho bridge(s) selected from the group consisting of formacetal, 3'-thioformacetal, methylhydroxyl-amine, oxime, methylenedimethylhydrazo, dimethylenesulfone and silyl; (c) complete or partial replacement of the sugar phosphate backbone by a morpholinonucleotide oligomer; (d) replacement of one, two, or three of the β-D-2'-deoxyribose units at the 5' end and/or at the 3' end by a member selected from the group consisting of α-D-2'-deoxyribose, L-2'-deoxyribose, 2'-F-2'deoxyribose, 2'—O-$(C_1-C_6)$alkyl-ribose, 2'-O-$(C_2-C_6)$-alkenyl-ribose, 2'-NH$_2$-2'-deoxyribose, β-D-xylofuranose, α-arabinofuranose, 2,4-dideoxy-β-D-eryt-hrohexopyranose, and carbocyclic, open-chain and bicyclo sugar analogs; and (e) complete or partial replacement of the natural nucleoside bases other than the natural nucleoside bases of the CAP regions by a member selected from the group consisting of 5-(hydroxymethyl) uracil, 5-aminouracil, pseudouracil, dihydrouracil, 5-($C_1$–$C_6$)-alkyl-ura-cil 5-($C_2$–$C_6$)-alkenyl-uracil, 5-($C_2$–$C_6$)-alkynyluracil-, 5-($C_1$–$C_6$)-alkyl-cytosine, 5-($C_2$–$C_6$)alkenyl-cytosine, 5-($C_2$–$C_6$)-alkynyl-cytosine, 5-fluorouracil, 5-fluorocytosine, 5-chiorouracil, 5-chlorocytosine, 5-bromouracil and 5-bromocytosine.

7. The oligonucleotide as claimed in claim 6, wherein in definition a) the modification is selected from the group consisting of a phosphorothioate, phosphorodithioate, (NR$^1$R$^2$)-phosphoramidate, phosphate-O-methyl ester, phosphate-O-ethyl ester, phosphate-O-isopropyl ester, methylphosphonate and phenylphosphonate bridge.

8. The oligonucleotide as claimed in claim 7, wherein the modification is selected from the group consisting of a phosphorothioate, phosphorodithioate and methylphosphonate bridge.

9. The oligonucleotide as claimed in claim 8, wherein the modification is a phosphorothioate bridge.

10. The oligonucleotide as claimed in claim 6, wherein in definition a) R$^1$ and R$^2$ independently represent hydrogen, ($C_1$–$C_4$)-alkyl or methoxyethyl.

11. The oligonucleotide as claimed in claim 6, wherein in definition b) the modification is selected from the group consisting of formacetal and 3'-thioformacetals.

12. The oligonucleotide as claimed in claim 6, wherein in definition b) the one, two or three phosphoric diester bridges are replaced at the 5' end and at the 3' end.

13. The oligonucleotide as claimed in claim 12, wherein the phosphoric diester bridges are replaced at the pyrimidine positions.

14. The oligonucleotide as claimed in claim 6, wherein in definition d) the modification is selected from the group consisting of 2'-F-2'-deoxyribose, 2'-O-($C_1$–$C_6$)alkylribose, 2'-O-($C_2$–$C_6$)alkenyl-ribose and 2'-NH$_2$-2'-deoxyribose.

15. The oligonucleotide as claimed in claim 14, wherein the modification is selected from the group consisting of 2'-F-2'-deoxyribose, 2'—O-($C_1$–$C_4$)alkyl-ribose, 2'—O-($C_2$–$C_4$)alkenyl-ribose and 2'-NH$_2$-2'-deoxy-ribose.

16. The oligonucleotide as claimed in claim 15, wherein the modification is selected from the group consisting of 2'—O-methyl-, 2'—O-allyl-, and 2'—O-butyl-ribose.

17. The oligonucleotide as claimed in claim 6, wherein in definition d) the one, two or three ribose units are replaced at the 5' end and at the 3' end.

18. The oligonucleotide as claimed in claim 17, wherein the ribose units are replaced at the pyrimidine positions.

19. The oligonucleotide as claimed in claim 6, wherein in definition e) the modification is selected from the group consisting of a 5-($C_1$–$C_6$)-alkyluracil, 5-($C_2$–$C_6$)-alkenyl-uracil, 5-($C_2$–$C_6$)-alkynyl-uracil, 5-($C_1$–$C_6$)-alkyl-cytosine, 5-($C_2$–$C_6$)-alkenyl-cytosine, 5-($C_2$–$C_6$)-alkynylc fluorouracil, 5-fluorocytosine, 5-chlorouracil, 5-chlorocytosine, 5-bromouracil, and 5-bromocytosine.

20. The oligonucleotide as claimed in claim 19, wherein the modification is selected from the group consisting of 5-($C_3$–$C_6$)-alkyl-uracil-, 5-($C_2$–$C_6$)-alkenyl-uracil, 5-($C_2$–$C_6$)-alkynyl-uracil, 5-($C_1$–$C_6$)alkyl-cytosine, 5-($C_2$–$C_6$)-alkenyl-cytosine, and 5-($C_2$–$C_6$)-alkynyl-cytosine.

21. The oligonucleotide as claimed in claim 20, wherein the modification is selected from the group consisting of 5-pentynylcytosine, 5-hexynyluracil, and 5-hexynylcytosine.

22. The oligonucleotide as claimed in claim 1, which is linked, at the 5' end and/or the 3' end to a molecule selected from the group consisting of polylysine, intercalators, fluorescent compounds, crosslinkers, lipophilic molecules, lipids, steroids, vitamins, polyethylene glycol, oligoethylene glycol, ($C_{12}$–$C_{18}$)-alkyl-phosphate diesters, and —O—CH$_2$—CH(OH)—O—($C_{12}$–$C_{18}$)-alkyl.

23. The oligonucleotide as claimed in claim 22 wherein the intercalator is selected from the group consisting of pyrene, acridine, phenazine and phenanthridine.

24. The oligonucleotide as claimed in claim 22 wherein the fluorescent compound is fluorescein.

25. The oligonucleotide as claimed in claim 22 wherein the crosslinker is selected from the group consisting of psoralene and azidoproflavin.

26. The oligonucleotide as claimed in claim 22 wherein the lipophilic molecule is ($C_{12}$–$C_{20}$)-alkyl.

27. The oligonucleotide as claimed in claim 22 wherein the lipid is 1,2-dihexadecyl-rac-glycerol.

28. The oligonucleotide as claimed in claim 22 wherein the steroid is cholesterol or testosterone.

29. The oligonucleotide as claimed in claim 22 wherein the vitamin is vitamin E.

30. The oligonucleotide as claimed in claim 1, which contains a 3'—3' inversion and/or a 5'—5' inversion at the 5' end and/or 3' end.

31. A process for preparing an oligonucleotide as claimed in claim 1, which comprises synthesizing the nucleotide sequence chemically from individual nucleotides.

32. A pharmaceutical composition comprising one or more oligonucleotides as claimed in claim 1 and a physiologically acceptable carrier.

* * * * *